United States Patent
Ağel et al.

(10) Patent No.: US 12,325,882 B2
(45) Date of Patent: Jun. 10, 2025

(54) **FAST AND PORTABLE MICROFLUIDIC DETECTION SYSTEM AS AN ALTERNATIVE TO *SALMONELLA'S* CLASSICAL CULTURE METHOD**

(71) Applicant: TUBITAK, Ankara (TR)

(72) Inventors: Hatice Esra Ağel, Kocaeli (TR); Şaban Yilmaz, Kocaeli (TR); Hasan Sağcan, Istanbul (TR)

(73) Assignee: TUBITAK, Ankara (TR)

( * ) Notice: Subject to any disclaimer, the term of this patent is extended or adjusted under 35 U.S.C. 154(b) by 1021 days.

(21) Appl. No.: 17/418,082

(22) PCT Filed: Dec. 25, 2019

(86) PCT No.: PCT/IB2019/061357
§ 371 (c)(1),
(2) Date: Jun. 24, 2021

(87) PCT Pub. No.: WO2020/136595
PCT Pub. Date: Jul. 2, 2020

(65) Prior Publication Data
US 2022/0098645 A1  Mar. 31, 2022

(30) Foreign Application Priority Data
Dec. 25, 2018  (TR) ................... 2018/20388

(51) Int. Cl.
*C12Q 1/689* (2018.01)
*B01L 3/00* (2006.01)
(Continued)

(52) U.S. Cl.
CPC ........ *C12Q 1/689* (2013.01); *B01L 3/502715* (2013.01); *B01L 7/52* (2013.01);
(Continued)

(58) Field of Classification Search
CPC .................................................... C12Q 1/689
See application file for complete search history.

(56) References Cited

U.S. PATENT DOCUMENTS 6,893,847 B2 * 5/2005 Yokoyama ............. C12Q 1/689
435/91.51
9,434,976 B2    9/2016 Yehualaeshet et al.

FOREIGN PATENT DOCUMENTS

CA      2768699      1/2011
CN      102424842    4/2012
(Continued)

OTHER PUBLICATIONS

Yang et al., Loop-Mediated Isothermal Amplification for *Salmonella* Detection in Food and Feed: Current Applications and Future Directions. Foodborne Pathog Dis. Jun. 2018;15(6):309-331. doi: 10.1089/fpd.2018.2445. PMID: 29902082; PMCID: PMC6004089 (Year: 2018).*

(Continued)

*Primary Examiner* — Aaron A Priest
*Assistant Examiner* — Tian Yu
(74) *Attorney, Agent, or Firm* — Crose Law LLC; Bradley D. Crose

(57) ABSTRACT

Every year, approximately 94 million cases of *Salmonella* gastroenteritis, with 155000 deaths, are reported each year and 85% of them reported to be food-borne. Investigation of the foods whether they are clean for *Salmonella* and sensitivity, easy applicability, absence of false positivity and negativity and the speed are the features sought in the analysis method for this investigation. It is not desirable for analysis to detect the presence of dead bacteria in food. Although the final product does not contain microbiologically harmful live bacteria during the food process, the detection of dead bacteria transmitted before the process causes the food product to be unfairly diagnosed as harmful. To prevent this situation, the analysis kits depending on molecular methods, increase their microorganism detection levels up to to $10^4$ while reducing their sensitivity. Since the molecular methods cannot discriminate dead and live organisms, a confirmation test is required to prove that the positive result of the analysis belongs to the live bacteria in the food, which results in additional cost and time loss. In the same way, it is necessary to verify whether the colonies that grow in the gold standard culture method, belong to *Salmonella* bacteria. In the developed system; $10^5$ dead bacterial DNA is eliminated in the food to prevent false positive results and the minimum detection limit is 10 bacteria. Also, in developed system, 4 primers specific to 6 regions of DNA are used. Therefore, the specificity of the method is very high (99.9%) and no verification test is needed. Since PCR systems require a device with complex temperature control units, they can make analysis in a laboratory-dependent manner. In the proposed system, DNA is amplified at constant temperature; no temperature cycle is required, therefore no complex instrument and laboratory infrastructure are required. All the procedures can be easily performed outside the laboratory on a portable mini-heater where pre-enrichment, DNA isolation from the sample and PCR steps are performed. For molecular analyses, the device is required to display the result of imaging or analysis. In the developed method, DNAs amplified by the loop-mediated isothermal DNA amplification method, are hybridized and combined with the labeled probe and then can be read by lateral flow method with the naked eye. As the results are visible by eye, no additional device is required. The classical culture method is accepted as the gold standard, but the duration of analysis is 7 days for positive samples, 3 days with verification test, for the molecular methods, and 5.5 hours including pre-enrichment time in the developed system.

2 Claims, 2 Drawing Sheets

Specification includes a Sequence Listing.

(51) Int. Cl.
  *B01L 7/00*    (2006.01)
  *C12Q 1/6853*  (2018.01)
  *C12R 1/42*    (2006.01)
  *B82Y 5/00*    (2011.01)

(52) U.S. Cl.
  CPC ........ *C12Q 1/6853* (2013.01); *B01L 2200/04* (2013.01); *B01L 2200/16* (2013.01); *B01L 2300/0819* (2013.01); *B01L 2300/0825* (2013.01); *B01L 2300/0829* (2013.01); *B82Y 5/00* (2013.01); *C12R 2001/42* (2021.05)

(56) References Cited

FOREIGN PATENT DOCUMENTS

| CN | 102424861 | | 4/2012 | |
|---|---|---|---|---|
| CN | 202626164 | | 12/2012 | |
| CN | 103320434 | | 9/2013 | |
| CN | 103627811 | | 3/2014 | |
| CN | 104263838 | | 1/2015 | |
| CN | 104830988 | | 8/2015 | |
| CN | 105950732 A | * | 9/2016 | ........... C12Q 1/6837 |
| CN | 107338291 | | 11/2017 | |
| CN | 107340389 | | 11/2017 | |
| CN | 107345961 | | 11/2017 | |
| CN | 107385019 | | 11/2017 | |
| CN | 107419007 | | 12/2017 | |
| WO | WO-2014104771 A1 | * | 7/2014 | ............ C12Q 1/689 |

OTHER PUBLICATIONS

Reyneke et al. Comparison of EMA-, PMA- and DNase qPCR for the determination of microbial cell viability. Appl Microbiol Biotechnol 101, 7371-7383 (2017) (Year: 2017).*

Fittipaldi et al. "Progress in understanding preferential detection of live cells using viability dyes in combination with DNA amplification." Journal of microbiological methods 91.2 (2012): 276-289. (Year: 2012).*

Fang et al., Propidium monoazide real-time loop-mediated isothermal amplification for specific visualization of viable *Salmonella* in food. Lett Appl Microbiol. Jul. 2018;67(1):79-88. doi: 10.1111/lam.12992. Epub May 8, 2018. PMID: 29665023 (Year: 2018).*

Park et al. An integrated rotary microfluidic system with DNA extraction, loop-mediated isothermal amplification, and lateral flow strip based detection for point-of-care pathogen diagnostics. Biosens Bioelectron. May 15, 2017;91:334-340. doi: 10.1016/j.bios.2016.11.063. Epub Dec. 14, 2016. (Year: 2016).*

Khodakov et al., DNA capture-probe based separation of double-stranded polymerase chain reaction amplification products in poly(dimethylsiloxane) microfluidic channels. Biomicrofluidics. Jun. 12, 2012;6(2):26503. doi: 10.1063/1.4729131 (Year: 2012).*

* cited by examiner

SEQUENCE LISTING

<160> NUMBER OF SEQ ID NOS: 5

<210> SEQ ID NO 1
<211> LENGTH: 20
<212> TYPE: DNA
<213> ORGANISM: Artificial Sequence
<220> FEATURE:
<223> OTHER INFORMATION: designed primer/probe

<400> SEQUENCE: 1

-continued

```
tcgatcagta ccagtcgtct                                                    20

<210> SEQ ID NO 2
<211> LENGTH: 19
<212> TYPE: DNA
<213> ORGANISM: Artificial Sequence
<220> FEATURE:
<223> OTHER INFORMATION: designed primer/probe

<400> SEQUENCE: 2
ataccggcct tcaaatcgg                                                     19

<210> SEQ ID NO 3
<211> LENGTH: 40
<212> TYPE: DNA
<213> ORGANISM: Artificial Sequence
<220> FEATURE:
<223> OTHER INFORMATION: designed primer/probe

<400> SEQUENCE: 3
acaacaaaac ccaccgccag gccggggaaa ttatcgccac                              40

<210> SEQ ID NO 4
<211> LENGTH: 40
<212> TYPE: DNA
<213> ORGANISM: Artificial Sequence
<220> FEATURE:
<223> OTHER INFORMATION: designed primer/probe

<400> SEQUENCE: 4
accaaaggtt cagaacgcgt cgccgggcat accatccaga                              40

<210> SEQ ID NO 5
<211> LENGTH: 19
<212> TYPE: DNA
<213> ORGANISM: Artificial Sequence
<220> FEATURE:
<223> OTHER INFORMATION: designed primer/probe

<400> SEQUENCE: 5
gtcttatctt gattgaagc                                                     19
```

FAST AND PORTABLE MICROFLUIDIC DETECTION SYSTEM AS AN ALTERNATIVE TO *SALMONELLA'S* CLASSICAL CULTURE METHOD

TECHNICAL FIELD

This invention is related to the microfluidic detection system of *Salmonella*, a pathogenic bacterium, by lateral flow method, that does not require a complex device and the results can be read by naked eye. Method allows the rapid, portable and laboratory environment independent diagnosis via Loop Mediated Isothermal Amplification (LAMP) with specifically designed primers, preventing false positivity by preventing the detection of dead bacteria, and preventing false negativity by detecting live but non-cultured (VBNC) bacteria.

It is a DNA based *Salmonella* detection system, alternative to gold standard classical culture method, that can differentiate dead-live bacteria, detect VBNC bacteria, do not require verification test after analysis and give fast and sensitive results. It can be used within the scope of public health, environmental health and food safety where dependence on laboratory environment and complex devices is removed.

STATE OF THE ART

Food pathogens are evaluated by various criteria, such as the virulance factor among themselves, the amounts that must be present in foods for virulance, the toxins they secrete. Many analysis methods are applied to identify and quantify these pathogens. However, there are some bacteria which develop a unique adaptation mechanism when confronted with unfavorable conditions for living and breeding. It is very difficult to detect such kind of bacteria; because they may have lost their ability to form colonies in solid media. This state is called a, Viable But Nonculturable, VBNC, state. *Salmonella* species, *Listeria monocytogenes*, *Escherichia coli* O157 are examples of microorganisms that can be pathogenic to humans in VBNC form. While some of these bacteria can carry pathogenic properties in VBNC state for a very short time, many of them lose their pathogenic properties. The absence of the necessary nutrients in the environment or exposure to cold, are the main factors that cause bacteria to become VBNC state. Bacterial cells in this state become more resistant to environmental conditions and can be cultured only when appropriate conditions are fulfilled. The VBNC definition is used in terminology for bacteria that cannot be recovered by culture methods but are viable and maintain their cellular activity. VBNC form is a physiological condition and mostly seen in Gram Negative bacteria; however, it is also possible for some Gram-positive bacteria. Cells in VBNC form are twice as resistant as cells in the logarithmic phase.

*Salmonella* poses a potential risk for public health in both vegetative and VBNC forms. Since bacteria cannot be produced on the plate by culture in VBNC form, the risk becomes even greater because the diagnosis is very difficult. Determination of the presence of VBNC microorganisms from contaminated water and foodstuffs by using the correct methods is of great importance for water and food safety. Methods for detecting VBNC cells are generally methods based on cellular activity or substrate production. In recent years, studies on VBNC bacteria have focused on the development of effective, practical and highly sensitive detection methods, and as a result, it has been emphasized that molecular techniques such as PCR and Real Time PCR are reliable methods. However, with these methods it cannot obtained exact, 100% accurate and reliable results. The biggest obstacle in molecular methods is the interference of dead bacteria with the results. However, it is possible to detect VBNC microorganisms that may cause poisoning in food by the use of chemicals that prevent the detection of the dead bacteria in the PCR stage by breaking them down to prevent their amplification. Deoxyribonuclease I (DNase I) nonspecifically breaks down single and double stranded DNA. In addition to DNase I, propodium monoazide (PMA) and ethidium monoazide (EMA) have recently been used to separate dead and live cells from each other. PMA; is a photo-reactive dye that binds to the DNA molecule. As the cell wall polarization of dead cells changes, it enters the cell and binds to dead bacteria DNA. It is activated by light and breaks the DNA molecule from where it binds. Since it cannot pass through the live bacteria cell wall, they cannot bind to and damage the live bacteria DNA. Therefore, dead bacterial DNAs cannot be replicated during PCR amplification. Chemicals like PMA, EMA, DNAse I were used separately for DNA elimination and the reaction limits of their use were not determined precisely in previous studies. Increased amounts of eliminated dead bacterial DNA have been reported in response to increased usage amounts of said chemicals. However, while the method subject to the patent was developed, it was found that after a certain level, the PMA and DNAse amounts had some consequences like inhibiting the reaction and damaging of the live bacteria. The developed method should be sensitive to the negative effects of live bacterial DNA during the amplification reaction while eliminating the dead bacteria. This means that the method should not damage the live bacterial DNA while the highest amount of dead bacterial DNA is eliminated. In order to stabilize this balance, DNase and PMA are used together, unlike the other methods described herein.

With the proposed DNA-based method, VBNC bacteria detection system, with the probes providing 100% specificity has been developed that do not require laboratory infrastructure, is portable, is capable of detecting *Salmonella*, pathogen from food in 5.5 hours including preenrichment process, and is able to eliminate dead bacteria, which do not cause food poisoning, more effectively, by this way preventing to false positivity in results.

In the state of the art;

In the Chinese patent document numbered CN103320434B, the primer set to be used with the LAMP method for the detection of *Salmonella* from food is reported. The evaluation of the results is carried out by using a device with fluorescent radiation. The patent does not include; the dead-live bacterial DNA separation, and a method of reading the result with the naked eye independently from the device in the evaluation step of analysis results by a lateral flow method. The primer set used is different. The portable mini-heater on which pre-enrichment, DNA isolation, and amplification is carried out is not covered by this patent.

Chinese patent document numbered CN103627811B relates to the use of the LAMP method for the rapid detection of *Salmonella* in meat products. Within the scope of this patent, the primer set that will work with the LAMP method and the working conditions are reported. Corresponding patent, does not include; the dead-live bacterial DNA separation, and a method of reading the result with the naked eye independently from the device in the evaluation step of analysis results by a lateral flow method. The primer set used is different. The portable miniheater on which pre-enrichment, DNA isolation, and amplification is carried out is not covered by this patent.

Chinese patent document numbered CN102424861B relates to an isothermic amplification method kit for the rapid detection of the *Salmonella* pathogen in foods, particularly targeting the HisJ gene region. Corresponding patent, does not include; the dead-live bacterial DNA separation, and a method of reading the result with the naked eye independently from the device in the evaluation step of analysis results by a lateral flow method. The primer set used is different. The portable mini-heater on which pre-enrichment, DNA isolation and amplification is carried out is not covered by this patent.

United States patent document numbered U.S. Pat. No. 9,434,976B2 describes a modified sample preparation method for the separation of dead/live bacteria in the PCR reaction. This method uses a substance called 5, 5'-(6, 22-dioxo-11, 14, 17-trioxa-7, 21-diazaheptacosane-1, 27-diyl) bis (3, 8-diamino-6-4 phenylphenanthridin-5-ium) iodide. This patent is a modified sample preparation method for the separation of dead/live bacteria in a PCR reaction. It does not include PMA+DNase I combination. The primer set used is different. The portable mini-heater, on which pre-enrichment, DNA isolation, and amplification is carried out, is not covered by this patent.

Canadian patent document numbered CA2768699C describes a method of distinguishing live cells from dead cells or injured cells in a test sample. The patent does not include the PM A+DNase I combination. The portable mini-heater, on which pre-enrichment, DNA isolation and amplification is carried out, is not covered by this patent.

The Chinese utility model document numbered CN202626164U relates to a device designed for the application of PMA and EMA for the removal of dead bacterial DNA. The device only allows the application of the halogen lamp for the activation of PMA/EMA. The utility model is only relevant for the application of the halogen lamp for the activation of PMA/EMA and does not include the PMA+DNase I combination. It is also not a device for pre-enrichment and DNA isolation. The portable mini-heater on which pre-enrichment, DNA isolation, and amplification is carried out is not covered by this patent.

Chinese patent document numbered CN107338291A relates to the method of detection by chromatographic biosensor using a loop mediated isothermal amplification primer specific to *Escherichia coli* 0157. The present method can be used to distinguish between live and dead bacterial cells. The patent object is directed to the detection of *E. coli* 0157 bacteria. The pre-enrichment step carried out with magnetic beads. The patent does not include the specific combination protocol of PMA/DNAse and dead/live bacteria DNA separation process. The chromatographic imaging method is with the classical LFD (Lateral Flow Device) method and differs from the lateral flow application in which the probe hybridization onto the surface in the microfluidic system and hybridization of positive DNA to this probe takes place at 65° C. The portable mini-heater, on which pre-enrichment, DNA isolation, and amplification is carried out is not covered by this patent.

Chinese patent document numbered CN107419007A relates to the method of detection by chromatographic biosensor using a loop mediated isothermal amplification primer specific for *Staphylococcus aureus*. The present method can be used to distinguish between live and dead bacterial cells. The objective of the patent is to detect *S. aureus* bacteria. The pre-enrichment step is carried out with magnetic beads. Patent, dead/alive the bacterial DNA separation process does not include the specific combination protocol of PMA/DNAse. The chromatographic imaging method is with the classical LFD method and differs from a lateral flow application in which the probe hybridization on the surface in the microfluidic system and hybridization of positive DNA to this probe takes place at 65° C. The portable mini-heater on which pre-enrichment, DNA isolation, and amplification is carried out is not covered by this patent.

Chinese patent document numbered CN107385019A relates to the method of detection by *Listeria*-specific loop mediated isothermal amplification primer by chromatographic biosensor. The present method can be used to distinguish between live and dead bacterial cells. The patent objective is to detect *Listeria* bacteria.

The pre-enrichment step is carried out with magnetic beads. The patent does not include the specific combination protocol of PMA/DNAse for dead/live bacteria DNA separation process. The chromatographic imaging method is with the classical LFD method and differs from a lateral flow application in which the probe hybridization on the surface in the microfluidic system and hybridization of positive DNA to this probe takes place at 65° C. The portable mini-heater, on which pre-enrichment, DNA isolation and amplification is carried out is not covered by this patent.

Chinese patent document numbered CN107345961A relates to a method of detection by chromatographic biosensor using a loop mediated isothermal amplification primer specific to *Enterobacter* sakazakii. The present method can be used to distinguish between live and dead bacterial cells. The object of the patent is to detect *E. sakazakii* bacteria. The pre-enrichment step is carried out with magnetic beads. The patent does not include the specific combination protocol of PMA/DNAse for dead/live bacteria DNA separation process. The chromatographic imaging method is with the classical LFD method and differs from a lateral flow application in which the probe hybridization on the surface in the microfluidic system and hybridization of positive DNA to this probe takes place at 65° C. The portable mini-heater on which pre-enrichment, DNA isolation, and amplification is carried out is not covered by this patent.

Chinese patent document numbered CN102424842B relates to methods of molecular biology detection of bacteria in the field of biotechnology, particularly in the detection of *Salmonella* LAMP method and kit specific primers. Corresponding patent, does not include; the dead-live bacterial DNA separation, and a method of reading the result with the naked eye independently from the device in the evaluation step of analysis results by a lateral flow method. The primer set used is different. The portable mini-heater on which pre-enrichment, DNA isolation and amplification is carried out is not covered by this patent.

Chinese patent document numbered CN104830988A discloses a method for detecting *Salmonella typhimurium* using LAMP primer and kit. *S. typhimurium* infection in veterinary clinical specimens can be quickly and accurately identified. Corresponding patent, does not include; the dead-live bacterial DNA separation, and a method of reading the result with the naked eye independently from the device in the evaluation step of analysis results by a lateral flow method. The primer set used is different. The portable mini-heater on which pre-enrichment, DNA isolation and amplification is carried out is not covered by this patent.

Chinese patent document numbered CN104263838A relates to a rapid detection kit and a detection method for *Listeria monocytogenes*. It is a method incorporating LAMP technology and LFD detection technology including kit composed of, specific primers and a specific probe, for detecting *L. monocytogenes*. Corresponding patent, does not include; the dead-live bacterial DNA separation, and a method of reading the result with the naked eye independently from the device in the evaluation step of analysis results by a lateral flow method. The portable miniheater on which pre-enrichment, DNA isolation, and amplification is carried out is not covered by this patent.

Chinese patent document numbered CN107340389A relates to a nucleic acid based biosensor chromatography method for the detection of *Salmonella* according to the virulence of the invA gene of *Salmonella*. The patent does not include the specific combination protocol of PMA/DNAse for dead/live bacteria DNA separation process. Chromatographic imaging is the classical LFD method. The patent is different from a lateral flow application where the hybridization of the probe on the surface and hybridization of positive DNA to this probe takes place at 65° C. in the microfluidic system. The primer set used is different. The portable miniheater on which pre-enrichment, DNA isolation, and amplification is carried out is not covered by this patent.

Technical Problem That the Invention Aims to Solve

In microbiology, the gold standard for the detection of infectious live bacteria is the classical culture method. The classical culture method has undesirable characteristics such as the fact that it cannot detect live but non-cultured bacteria, and it needs the longer analysis period. In food samples *Salmonella* analysis with classical method takes 5 days for negative results and 7 days for positive results. This period is too long to be accepted especially in places where there is large amounts of food production and consumption affecting public health and in the analysis of exported and imported products. Molecular techniques that shorten this period gradually began to be used instead of the classical culture method. But a molecular method like Real time PCR is also detect dead bacteria and thus cause false positive results. To avoid the worry of false positive results in Real Time PCR analysis; Verification testing is required after analysis by the conventional method, which means the prolongation of analysis time in samples that result in positive results. Real-time PCR methods amplify DNA products using thermal cycling as in the traditional PCR method. This causes the continues change of device's temperature which resulted in the prolonged amplification time for the proliferation of DNA product.

In the system subject to the patent, it is possible to save time as a result of the use of loop-based isothermal DNA amplification by applying heat at one point with specially designed primers, distinctly from the different temperature cycles required in Real Time PCR. In the used LAMP method, as 100 times more amplification product is formed than the PCR method, it was observed that the 4 hours of pre-enrichment time could be enough.

The method for the detection of VBNC forms should be at a sensitivity level that eliminates dead bacteria while not affecting live bacterial DNA during the amplification reaction. That is, it should not damage the live bacterial DNA while eliminating the highest amount of dead bacteria DNA. To achieve this balance, the combination of DNAse and PMA was used in the system developed, unlike the other described methods. In other studies, DNase and PMA were applied separately and not studied together. Studies have shown that the use of more than 50 μM of PMA leads to inhibition of loop-based isothermal amplification reaction. When 50 μM was used, it was found that PMA was not able to eliminate enough dead bacteria DNA. Also, the highest DNAse I concentration was found to be 50 U per sample to eliminate the dead bacteria DNA in the appropriate amount ($10^4$ bacteria) and to prevent damage to live bacteria. With the present invention, this has been overcome by the use of DNAse I together with PMA. PMA is more effective in areas where DNAse I cannot reach, but PMA is more effective when the cell is dead but the cell membrane is not completely disintegrated. DNAse I was found to be more effective than PMA to break free DNAs. The combination of DNAse and PMA yields better results than the use of much larger amounts of them separately.

With the proposed system, the results will be faster than the DNA based diagnostic kits on the market and with the same reliability and sensitivity as the gold standard classical culture method. In developed system, amplification of the pathogen DNA is carried out by loop-based isothermal amplification (LAMP). Since the LAMP method uses 4 or 6 different primers that detect 6 different regions on the target gene, the sensitivity of the method is much higher than that of conventional PCR methods. Also, Notomi et al. (2000) showed that the amount of LAMP products are 100 times more than traditional PCR products realized in the same period. This shortens the amplification reaction time and allows the product, which can be detected by the microchip at the $50^{th}$ minutes of conventional PCR, to be detected at the $20^{th}$ minutes of the LAMP reaction. It is not desirable to detect the presence of dead bacteria in food. Although the final product does not contain microbiologically harmful live bacteria during the food process, the detection of dead bacteria transmitted before the process causes the food product to be unfairly diagnosed as harmful. In order to prevent this situation, the sensitivity of the kits which are analyzed by molecular method is decreased by increasing the limit of detection (LOD). In the developed system, detection limits were not increased and thus sensitivity of the system was not decreased due to the proper use of PMA and DNAse I and optimal pre-enrichment time. The detection limit of the system is well below the number of microorganisms that can cause disease when food is consumed, and can detect ≤10 bacteria in the food taken for analysis.

The operating time of the system is 1 hour+30 minutes. However, a pathogen analysis requires 16-24 hours of pre-enrichment to find one living bacteria in food. In the proposed system, the total analysis time is five and a half (5.5) hours since 4 hours of pre-enrichment will be sufficient in the targeted system. The pre-enrichment process of the DNA-based kits available in the market is 1 day (16-24 hours) and the system has a working time of one and a half (1.5) hours and additional 1 day is required for the verification of positive samples. Therefore, two and a half (2.5) days are required with molecular based kits in the market. In the proposed system, even in positive samples, including the pre-enrichment step, a total of 5.5 hours will be sufficient.

Real Time PCR is a method that should be studied in the laboratory with device. Real-time PCR systems are capable of displaying DNA replication and performing temperature cycles instantaneously. Since they have units capable of detecting fluorescent radiation and conducting complex heating, these devices are rough and laboratory dependent. Furthermore, since the detection of amplification products is carried out using fluorescent dyes, the method is susceptible to inhibitions and therefore the need for specialized personnels is high. Developed system does not depend on laboratory infrastructure and complex devices in all stages from preparation to analysis of food sample to the taking of results. The kit, containing a portable mini-heater on which the pre-enrichment, DNA isolation and LAMP reaction is carried out, and an analysis solutions is ready in a box.

System; does not require complex device-laboratory infrastructure and expertise, portable, accurate, speedy, efficient, specific, sensitive and easily applicable.

DESCRIPTION OF THE FIGURES

The figures are provided for a better understanding of the subject matter of the patent and the scope of the patent it is not limited with these figures.

DESCRIPTION OF REFERENCES IN THE FIGURES

Figure 1:
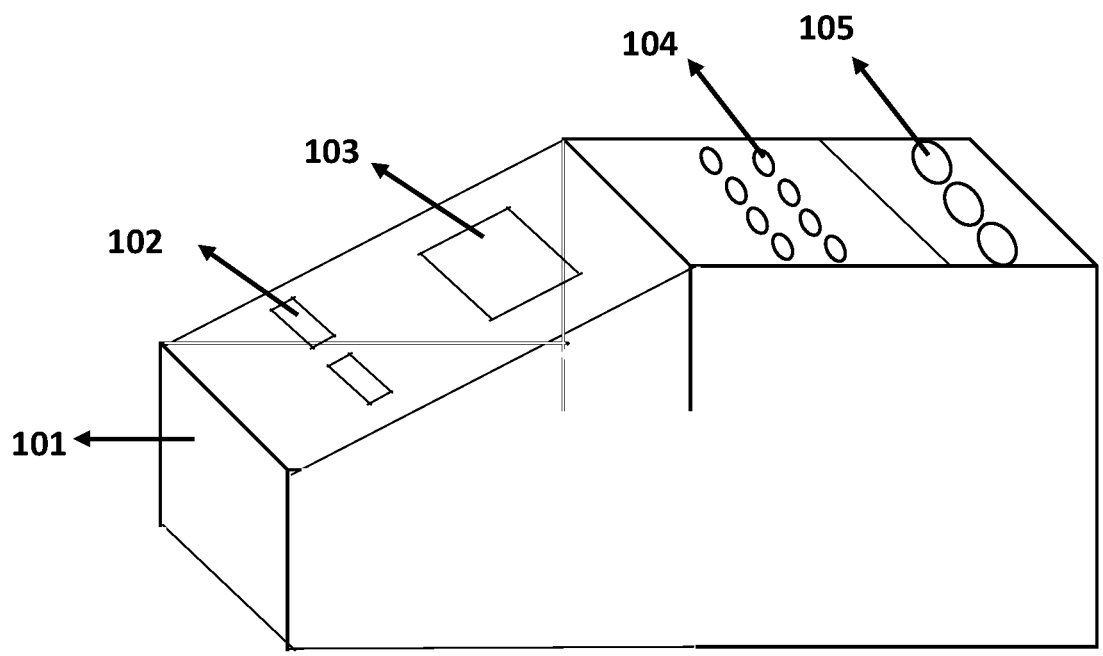
FIG. 1. A portable mini heater and analysis cassette on which example pre-enrichment, DNA isolation and DNA amplification processes takes place.

Parts shown in the figures are numbered one by one, It is given.

101: Mini heater
102: Cassette inlet
103: Touch Screen Display
104: 1.5 ml tube inlet
105: 50 ml tube inlet
201: Disposable analysis cassette
202: Sample loading opening
203: Amplification well
204: Switch
205: Hybridization channel
206: Hand holding portion

DISCLOSURE OF THE INVENTION

Developed system is a kit containing the portable mini heater (FIG. 1) where the preenrichment, DNA isolation and LAMP reaction takes place, analysis cassette (FIG. 2) and analysis solutions. Kit is ready to use in a box. Loop mediated isothermal DNA amplification reaction in itself can be controlled by negative, positive and inhibition controls. Invention kit content included; Dead/live bacteria DNA separation solutions (PMA and DNAse I), *Salmonella* isothermal DNA amplification primer set (10× Primary Mix, 2 μM F3, 2 μM B3, 16 μM FIP and 16 μM BIP) and lateral flow result in display cassette.

In the sample preparation step; incubation of sample placed in peptone water, liquid nutrient media or any other nutrient media used for similar purposes, in the well (105) shown in FIG. 1 for 4 hours at 37° C. in a 50 ml tube, to ensure the growth of bacteria in tubes without distrtupting the 1/9 sample-medium ratio is within the scope of this patent.

To separate dead and live cells during the pre-enrichment stage, an optimized PMA/DNase I; a protocol for the removal of dead bacterial DNA was developed. Combined application of DNAse I and PMA, for the destruction and removal of dead bacterial DNA found in the sample, is within the scope of this patent. PMA and DNAse I can be applied in different orders for the Dead/Live separation. Application of DNAse I 25U, at 37° C., 30 min; and PMA 10 μM, in the dark at, at 25° C., 7 min. is within the scope of this patent. The use of PMA at a concentrations of 5 μM and more and the incubation in room temperature and dark environment are also within the scope of this patent. For DNA isolation, Proteinase K can be used at a concentration of 10 mg/ml or more and 30 μl or more. Solutions, prepared with different concentrations of Tris- HCl, KCl, and MgCl$_2$ can be used in the pH range of 7-9.

Primers specific to the InvA gene were specifically designed to enrich the *Salmonella* pathogen with the LAMP method. Primer Explorer V5 program was used to design the primers.

The sequences of the designed external forward (F3), external reverse (B3), internal forward (FIP) and internal reverse (BIP) primers are given sequentially in 5'-3' direction;

F3 comprising the nucleotide sequence SEQ ID NO: 1,
B3 comprising the nucleotide sequence SEQ ID NO: 2,
FIP comprising the nucleotide sequence SEQ ID NO: 3,
BIP comprising the nucleotide sequence SEQ ID NO: 4.

The FIP primer is marked with FAM at the 5' end. The molar ratios of the primers used in the reaction (external primers; internal primers) are: 1-4: 2-8: 4-16. As a DNA polymerase, Bst polymerase enzyme is used because of its strand displacement property. MgSO$_4$ concentration is 4 mM, dNTP concentration is 0.4 mM, Bst polymerase amount is 2U. DNase and RNAse free ddH$_2$O is used as a negative control.

Detection can be achieved if there is a genome that can be amplified for the loop-mediated isothermal DNA amplification reaction. Pre-enrichment can be kept short for fast-breeding bacteria (ones have short doubling time).

If the amount of contamination is high, the method can yield directly just by DNA isolation, without no need to pre-enrichment. If the amount of contamination is high or if the sample is taken directly from the main reserve (e.g. wash water); instead of DNA isolation, the sample can also be transferred directly to the reaction tube after a short lyse. Once DNA has been isolated from the food sample, confirmation could be done repeatedly by LAMP reaction.

For molecular analyses, the device is required for visualization or the display of analysis results. Lateral flow devices (LFD), which are also test method itself, have recently begun to be used for visualization of the results of molecular analyses. In the developed method, specially designed DNA probes, that identify the target DNA, were hybridized to the lateral flow visualization cassettes.

In the developed lateral flow system, as it could be possible to evaluate results by naked eye with the help of gold nanoparticles, throught the probe hybridization on the surface and a lateral flow application where hybridization of positive DNA to this probe takes place at 65° C., no additional device is needed.

The use of bst enzyme or a different enzyme with DNA strand opening capability for DNA amplification, the incubation of samples for different periods in the range of 60-75° C. for DNA amplification and the carrying out of this process in a portable mini heater specially designed for the disposable cassette (FIG. 1), is within the scope of this patent.

FIG. 1 depicts the device that can be charged and operated without the need for continuous connection to the electrical source, on which pre-enrichment, DNA isolation, and DNA amplification can be performed. The device has three 50 ml (105), six 2-1.5 ml tube inlets (104) and two diagnostic cassette inlets (102). It also has a touch screen display (103) where the controls can be conducted. The device is suitable for operation in the 0-100° C. range.

Figure 2:
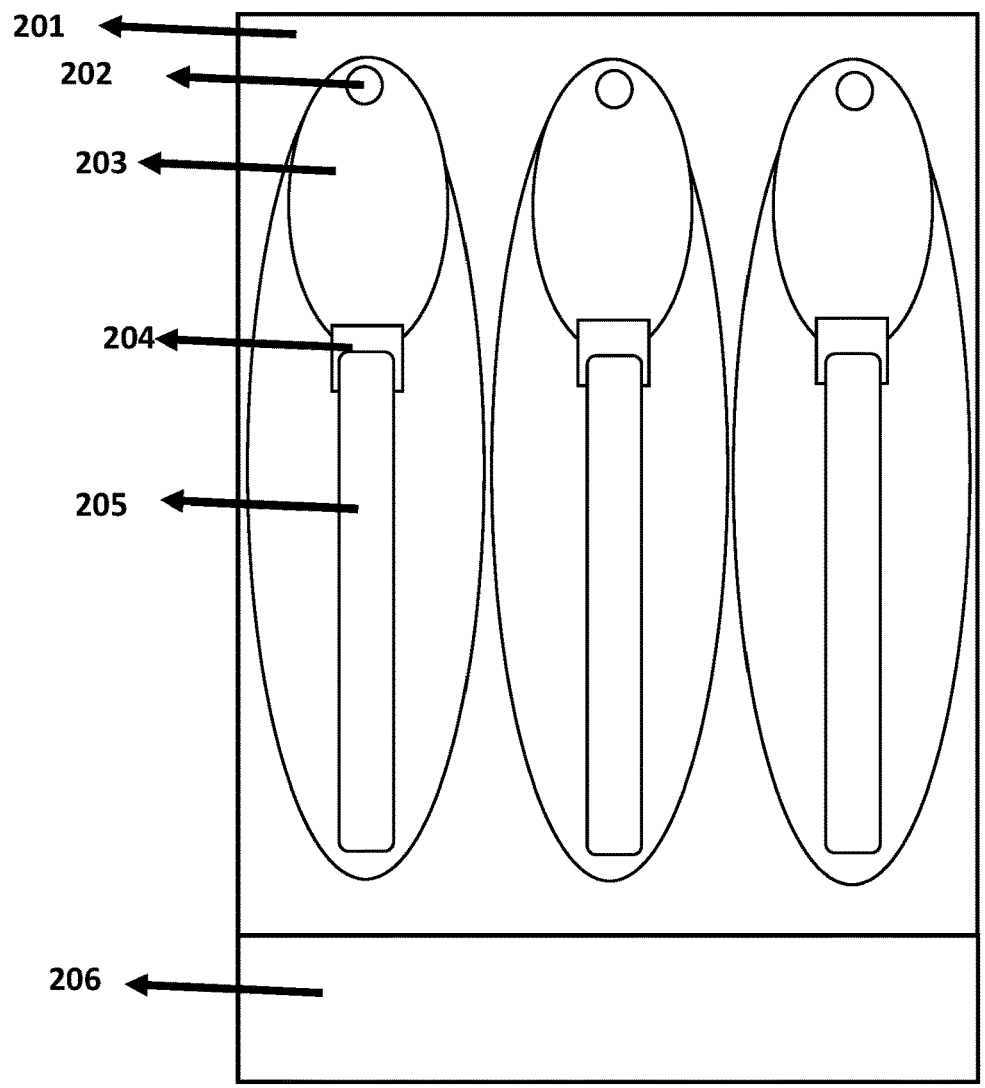
FIG. 2. is a top view of the analysis cassette.
Figure 3:
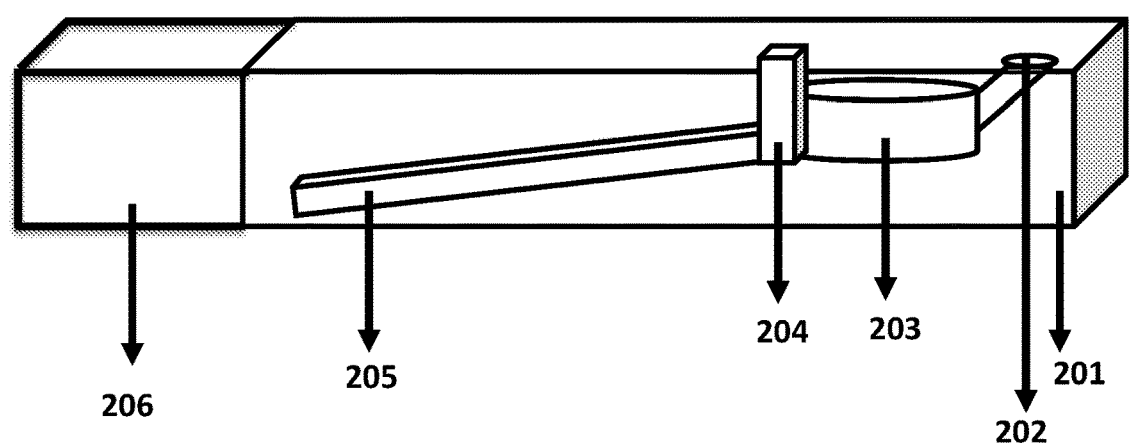
FIG. 3. is a side view of the analysis cassette.

FIG. 2 shows a single-use analysis cassette in which DNA amplification takes place, as well as the results can be displayed. Generally, it is composed of the amplification well (203) where the amplification takes place and the microfluidic hybridization channel where the result is displayed (205). The cassette is provided with a sample loading opening (202) to which the sample is loaded into the amplification well, a switch (204) for carrying the amplification product to the hybridization channel, and a hand holding portion (206).

The amplification well (203) offers a capacity of 200 µl. It also has an opening for delivering the reaction mixture to the amplification well. There is a lock system between the well and the channel. After the amplification period, the amplicons can be transferred to the channel by pressing the switch (204) to perform the diagnostic process. By designing the hybridization channel (205) inclined, the flow can be achieved without the need for any additional device (pump). There are two bands in the microfluidic channel: control and test. The test band contains the pathogen-specific DNA probe to be diagnosed, while the control band contains the antibody that recognizes the gold nanoparticles indicating that the system is operating.

The use of a probe hybridized microfluidic system and the use of a probe as 5 µmol or more is also within the scope of patent protection. The alignment of the original probe attached to the surface is given with the nucleotide sequence SEQ ID NO: 5.

The hybridized sample and the phosphate buffer (hybridization buffer) containing 1% BSA can be used at different concentrations. In the disposable cassette which is used for diagnosis (FIG. 2), the hybridization surface may be nitrocellulose, SU-8, PDMS or glass. The analysis cassette consists of two different parts on which amplification, and hybridization takes place separately. During the amplification, new FAM labeled products will be formed with the help of FAM (Fluorescein) labeled FIP. The two parts of cassette are connected by a simple collapsible switch (204). After amplification, the switch opens and the FAM-labeled product interacts with the anti-FAM antibody in the hybridization zone with the hybridized gold nanoparticle buffer. Because the cellulose membrane or hybridization portion is inclined, the product will travel along the path. During this process, the hybridization channel is heated to 65° C. to allow hybridization between the product and the probe that is specific to the target DNA sequence. In positive samples, visual result evaluation is possible with the accumulation of amplification products containing gold nanoparticle with anti-FAM antibody in the band where the probe is located. Anti-rabbit Antibody was hybridized to the surface as a control band. As a result of the reaction, gold nanoparticles with free anti-FAM antibody hybridize to the control band.

This indicates that the system is running. The specificity of the probe is 100%.

Sample Application

I.
In a 50 ml tube, 1/9 ratio of peptone/water is put, and 5 g of homogenized food samples are added. The tube is incubated for 4 hours at 37° C. in the device shown in FIG. 1 for preenrichment.

II.
After 4 hours, the tube is homogenized by hand shaking and 1.5 ml sample is taken into a 2 ml centrifuge tube. The samples are centrifuged at 8000 rpm for 3 minutes using a portable mini-centrifuge. The supernatant is discarded. 25U DNAse I and 100 µl DNAse I buffer were added onto the precipitate. Let it stand for 30 minutes at 37° C. in the device shown in FIG. 1. Then 5-50 µM PMA (Biotium 10 Inc. USA) was added and incubated for 5 minutes in the dark at room temperature. Finally, it is kept under agitation for 2 minutes on ice at 20 cm distance under a 650W halogen lamp.

III.
Samples are centrifuged at 8000 rpm for 3 minutes to discard the supernatant and 30 µl proteinase K (20 mg/ml) and 100 µl solution A (10-100 mM Tris-HCl, 10-100 KCl, 1-10 mM MgCl, pH 8.2) is added. The samples are stored in a mini-heater as shown in FIG. 1 for 20 minutes at room temperature, then for 10 minutes at 90-100° C. The top phase is used as a DNA sample after centrifugation at the last speed for 5 minutes with the help of portable mini centrifuge.

IV.
The loop-mediated isothermal DNA amplification reaction is prepared for diagnosis. Per reaction; IX reaction buffer (NEB, USA), 1-10 mM $MgSO_4$, 1-5 mM dNTP, 1-2 µM FIP/BIP, 0.1-1 µM F3/B3 primers, 50-500 U/ml Bst 3.0 DNA polymerase, 5 µl of DNA and $ddH_2O$ until complete to 25 µl reaction mix, are added. In the amplification well (203) where the reaction will take place, the DNA is incubated for 1 hour at 60-72° C. for amplification. It is then incubated for 20 minutes at 80° C. for enzyme inactivation in the device shown in FIG. 1.

After DNA amplification, 100 µl of hybridization buffer is added to the sample and passed through the microfluidic channel where the *Salmonella* probe is hybridized at the temperature in the range of 60-70° C. through the device shown in FIG. 1. The result is observed within 5 minutes.

INDUSTRIAL APPLICATION OF THE INVENTION

The aforementioned microfluidic detection system has; high accuracy, speed, efficiency, specificity and sensitivity, easy applicability, portability, no need for complex devices and it issued for import and export quarantine site detection, food hygiene and inspection. It is also important in foodstuff kitchens, in mass consumption points, and in individual food safety guarantee, because of being portable.

The invention claimed is:

1. A *Salmonella* pathogen detection method, characterized in that the method comprises following process steps;
   a. sample preparation and pre-enrichment, completed in 4 hours,
   b. separation of dead and live bacteria, by the application of DNase I 25U, at 37° C. for 30 min; and PMA 5-50 μM, in the dark, at 25° C. for 7 min, in no particular order,
   c. DNA isolation where, Proteinase K and solution A comprising 10-100 mM Tris-HCl, 10-100 KCl, 1-10 mM MgCl2, pH 8.2 are applied together,
   d. Loop-mediated isothermal DNA amplification with 4 primers which are F3, B3, FIP, BIP primers comprising nucleotide sequence SEQ ID NOs:1, 2, 3, and 4 respectively and the 5' end of the FIP primer is marked with FAM, specifically designed for InvA gene,
   e. hybridization of amplicons from Step (d) with unique probe which is comprising nucleotide SEQ ID NO: 5, is attached in single-use disposable cassettes, which are hybridized in disposable cassettes, and evaluation of results with naked eye,
   f. after performing steps a-e, display result on a portable mini-heating device.

2. The method according to claim 1 characterized in that, surface to which the probe is attached is PDMS.

* * * * *